(12) United States Patent
Whitchurch et al.

(10) Patent No.: US 7,939,701 B2
(45) Date of Patent: May 10, 2011

(54) AROMATIC ISOMERIZATION CATALYST AND A PROCESS OF USE THEREOF

(75) Inventors: Patrick C. Whitchurch, Bossier City, LA (US); Paula L. Bogdan, Mount Prospect, IL (US); Terrence E. Deak, Chicago, IL (US); Dimitri A. Trufanov, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 779 days.

(21) Appl. No.: 11/954,296

(22) Filed: Dec. 12, 2007

(65) Prior Publication Data

US 2011/0077146 A1    Mar. 31, 2011

(51) Int. Cl.
*C07C 5/22*    (2006.01)
*B01J 29/06*    (2006.01)

(52) U.S. Cl. ........ 585/481; 585/477; 585/480; 585/482; 502/60; 502/63; 502/64; 502/66; 502/78; 502/79

(58) Field of Classification Search .............. 502/60, 502/63, 64, 66, 74, 77, 78, 79; 585/477, 585/480, 481, 482
See application file for complete search history.

(56) References Cited

U.S. PATENT DOCUMENTS

| | | | |
|---|---|---|---|
| 4,427,790 A | 1/1984 | Miale et al. | |
| 4,500,420 A | 2/1985 | Miale et al. | |
| 4,556,646 A | 12/1985 | Bezman | |
| 4,665,255 A | 5/1987 | Chang et al. | |
| 6,037,294 A | 3/2000 | Drake et al. | |
| 6,143,941 A | 11/2000 | Sharma et al. | |
| 6,239,056 B1 | 5/2001 | Gajda et al. | |
| 6,355,853 B1 | 3/2002 | Sharma et al. | |
| 6,388,149 B2 | 5/2002 | Rühl et al. | |
| 6,512,155 B1 | 1/2003 | Johnson et al. | |
| 6,872,866 B1 | 3/2005 | Nemeth et al. | |
| 7,125,529 B2 | 10/2006 | Ablin | |
| 7,314,601 B2 | 8/2007 | Negiz et al. | |
| 7,456,125 B2 | 11/2007 | Bogdan et al. | |
| 2001/0008949 A1* | 7/2001 | Wu et al. ................ | 585/420 |
| 2005/0153829 A1* | 7/2005 | Nemeth et al. ............ | 502/67 |
| 2007/0060470 A1* | 3/2007 | Bogdan et al. ............ | 502/60 |
| 2007/0060779 A1 | 3/2007 | Bogdan et al. | |
| 2007/0259780 A1* | 11/2007 | Bogdan et al. ............ | 502/305 |

FOREIGN PATENT DOCUMENTS

JP    5-76770    3/1993
SU    1 774 553 A1    9/1995

OTHER PUBLICATIONS

Aleksandrova et al., Abstract of SU 1 774 553 A1, Sep. 10, 1995, Publisher: Derwent Information LTD.
Toyo Kogyo Co., Abstract of JP 5-76770, Mar. 30, 1993, Publisher: Derwent Information LTD.

* cited by examiner

Primary Examiner — Elizabeth D Wood
(74) Attorney, Agent, or Firm — David J Piasecki

(57) ABSTRACT

One exemplary embodiment can be an ion-exchanged xylene isomerization catalyst. The ion-exchanged xylene isomerization catalyst can include:
  about 1-about 99%, by weight, of at least one of MFI, MEL, EUO, FER, MFS, MTT, MTW, TON, MOR, and FAU zeolite;
  about 1-about 99%, by weight, of a binder having an aluminum phosphate; and
  no more than about 350 ppm, by weight, of a noble metal based on the weight of the catalyst. Generally, the catalyst has a quotient of (CO area)/(weight % of the noble metal) of no more than about 0.10.

20 Claims, No Drawings

AROMATIC ISOMERIZATION CATALYST AND A PROCESS OF USE THEREOF

FIELD OF THE INVENTION

The field of this invention generally relates to a catalyst for a C8 aromatic isomerization process or zone.

BACKGROUND OF THE INVENTION

The xylenes, such as para-xylene, meta-xylene and ortho-xylene, can be important intermediates that find wide and varied application in chemical syntheses. Generally, para-xylene upon oxidation yields terephthalic acid that is used in the manufacture of synthetic textile fibers and resins. Meta-xylene can be used in the manufacture of plasticizers, azo dyes, and wood preservers. Generally, ortho-xylene is a feedstock for phthalic anhydride production.

Xylene isomers from catalytic reforming or other sources generally do not match demand proportions as chemical intermediates, and further comprise ethylbenzene, which can be difficult to separate or to convert. Typically, para-xylene is a major chemical intermediate with significant demand, but amounts to only 20-25% of a typical C8 aromatic stream. Adjustment of an isomer ratio to demand can be effected by combining xylene-isomer recovery, such as adsorption for para-xylene recovery, with isomerization to yield an additional quantity of the desired isomer. Typically, isomerization converts a non-equilibrium mixture of the xylene isomers that is lean in the desired xylene isomer to a mixture approaching equilibrium concentrations. It is also desirable to convert ethylbenzene to one or more xylenes while minimizing xylene loss. Moreover, other desired aromatic products, such as benzene, can be produced from such processes.

Various catalysts and processes have been developed to effect xylene isomerization. In selecting appropriate technology, it is desirable to run the isomerization process as close to equilibrium as practical in order to maximize the yield of the desired isomer as well as produce other desired aromatic products, such as benzene. However, greater isomerization activity can be associated with a greater production of undesired side products. Generally, it is desirable to have a catalyst with sufficient activity to isomerize xylenes yet not produce undesired side products that can lower the purity of desired products, such as para-xylene and benzene. Thus, a catalyst having a favorable balance of activity, selectivity, and stability would be beneficial.

BRIEF SUMMARY OF THE INVENTION

One exemplary embodiment can be an ion-exchanged xylene isomerization catalyst. The ion-exchanged xylene isomerization catalyst can include:
about 1-about 99%, by weight, of at least one of MFI, MEL, EUO, FER, MFS, MTT, MTW, TON, MOR, and FAU zeolite; about 1-about 99%, by weight, of a binder having an aluminum phosphate; and
no more than about 350 ppm, by weight, of a noble metal based on the weight of the catalyst. Generally, the catalyst has a quotient of (CO area)/(weight % of the noble metal) of no more than about 0.10.

Another exemplary embodiment can be an ion-exchanged xylene isomerization catalyst. The ion-exchanged xylene isomerization catalyst can include:
about 20-about 90%, by weight, of an MFI zeolite;
about 10-about 90%, by weight, of an aluminum phosphate binder; and
about 150-about 350 ppm, by weight, of platinum based on the weight of the catalyst. Generally, the catalyst has a quotient of (CO area)/(weight % of platinum) of no more than about 0.10.

A further exemplary embodiment can be a process for isomerizing a non-equilibrium feed mixture of one or more xylenes and ethylbenzene. The process can include:
contacting the feed mixture with an ion-exchanged xylene isomerization catalyst to obtain an isomerized product having a higher proportion of para-xylene than in the feed mixture. Moreover, the ion-exchanged xylene isomerization catalyst can further include:
about 1-about 99%, by weight, of at least one of MFI, MEL, EUO, FER, MFS, MTT, MTW, TON, MOR, and FAU zeolite;
about 1-about 99%, by weight, of a binder having an aluminum phosphate; and
no more than about 350 ppm, by weight, of platinum based on the weight of the catalyst. The catalyst can have a quotient of (CO area)/(weight % of platinum) of no more than about 0.10.

Therefore, the catalyst can provide a favorable balance of activity, selectivity, and stability. Particularly, the catalyst can isomerize xylenes and ethylbenzene to obtain a desired isomer, such as para-xylene, while also decreasing the yield of undesired side products. These benefits can result in the production of a higher purity of other desired products, such as benzene. Moreover, such benefits can be obtained without the addition of noble metal modifiers, such as tin, rhenium or molybdenum.

DEFINITIONS

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated C1, C2, C3 . . . Cn where "n" represents the number of carbon atoms in the hydrocarbon molecule.

As used herein, the term "aromatic" can mean a group containing one or more rings of unsaturated cyclic carbon radicals where one or more of the carbon radicals can be replaced by one or more non-carbon radicals. An exemplary aromatic compound is benzene having a C6 ring containing three double bonds. Other exemplary aromatic compounds can include para-xylene, ortho-xylene, meta-xylene and ethylbenzene. Moreover, characterizing a stream or zone as "aromatic" can mean one or more different aromatic compounds.

As used herein, the term "support" generally means a molecular sieve that has been combined with a binder before the addition of one or more additional catalytically active components, such as a noble metal, or a subsequent process such as reducing or sulfiding.

As used herein, the term "catalyst precursor" generally means a support having the addition of one or more additional catalytically active components, such as a noble metal, but not subjected to subsequent processes, such as reducing or sulfiding, to complete the manufacture of the catalyst. However, in some instances, a catalyst precursor may have catalytic properties and can be used as a "catalyst".

As used herein, the term "ion-exchanged catalyst" generally means a catalyst subjected to an ion-exchange process after metal impregnation.

DETAILED DESCRIPTION OF THE INVENTION

A catalyst disclosed herein has sufficient activity to isomerize a non-equilibrium feed mixture of one or more xylenes to a desired xylene isomer while not producing excessive amounts of undesired side products. As such, a process utilizing such a catalyst can produce relatively pure streams of products, such as benzene, in addition to the desired xylene isomer.

A catalyst disclosed herein can include an acidic molecular sieve having a pore diameter of from about 4-about 8 angstroms, platinum and optionally tin in an amorphous aluminum phosphate binder. An example of a molecular sieve can include those having $Si:Al_2$ ratios greater than about 10:1, and often greater than about 35:1 or about 40:1, such as an MFI, MEL, EUO, FER, MFS, MTT, MTW, TON, MOR and FAU zeolite. A pentasil zeolite such as MFI, MEL, MTW or TON is preferred, and an MFI zeolite, such as ZSM-5, silicalite, Borolite C, TS-1, TSZ, ZSM-12, SSZ-25, PSH-3, or ITQ-1 may be especially preferred. Furthermore, two or more of the above zeolites can be used in combination.

Generally, the zeolite is combined with a binder for convenient formation of one or more catalyst particles. The proportion of zeolite in the catalyst may range from about 1-about 99%, by weight, preferably about 2-about 90%, by weight, more preferably about 10-about 90%, by weight, and optimally about 20-about 90%, by weight, or even about 20-about 50%, by weight.

Generally, the binder includes an amorphous phosphorous-containing alumina (herein referred to as aluminum phosphate). Typically, the atomic ratios of aluminum to phosphorus in the aluminum phosphate binder/matrix generally range from about 1:10-about 100:1, and desirably from about 1:5-about 20:1. The aluminum phosphate can have a surface area of up to about 450 $m^2$/gram, and preferably the surface area is up to about 250 $m^2$/g. The proportion of binder in the catalyst may range from about 1-about 99%, by weight, and preferably about 10-about 90%, by weight.

The catalyst may contain one or more other components. These components can be in amount of less than about 40%, by weight, and preferably less than about 15%, by weight, based on the catalyst weight. These components can include: (1) a refractory inorganic oxide such as an alumina, a titania, a zirconia, a chromia, a zinc oxide, a magnesia, a thoria, a boria, a silica-alumina, a silica-magnesia, a chromia-alumina, an alumina-boria, a silica-zirconia, or a phosphorus-alumina; (2) a ceramic, a porcelain, or a bauxite; (3) a silica or silica gel, a silicon carbide, a synthetically prepared or naturally occurring clay or silicate, optionally acid treated, as an example, an attapulgite clay, a diatomaceous earth, a fuller's earth, a kaolin, or a kieselguhr; or (4) a combination of materials from one or more of these groups.

Furthermore, the catalyst may contain a halogen component. The halogen component may be fluorine, chlorine, bromine or iodine or a mixture thereof, with chlorine being preferred. Generally, the halogen component is present in a combined state with the inorganic-oxide support. The optional halogen component is preferably well dispersed throughout the catalyst, that may include about 0.2-about 15%, by weight, calculated on an elemental basis. The halogen component may be incorporated in the catalyst composite in any suitable manner, either during the preparation of the inorganic-oxide support or before, while or after other catalytic components are incorporated. However, the catalyst preferably contains no added halogen other than that associated with other catalyst components.

The catalyst can include a noble metal, such as ruthenium, rhodium, palladium, osmium, iridium, and platinum. Preferably, the noble metal is platinum. The noble metal may exist within the final catalyst composite as a compound such as an oxide, a sulfide, a halide, or an oxysulfide; as an elemental metal; or as a combination with one or more other ingredients of the catalyst. Preferably, all the noble metal exists in a reduced state. Desirably, the platinum component is deposited in the molecular sieve. The concentration of noble metal, such as platinum, (calculated on an atomic basis) is typically no more than about 350, preferably 150-about 350, and optimally about 300-about 350, weight-ppm based upon the weight of the catalyst.

The catalyst may also include an IUPAC Group 14 element. Preferably, the IUPAD Group 14 element is tin. Often, the amount of tin (calculated as atomic tin) is in an atomic ratio to platinum in the catalyst of between about 1.2:1-about 30:1, preferably about 1.5:1-about 25:1, and in some instances from about 1.5:1-about 5:1.

The catalyst may also contain one or more metal components or modifiers. Such metal modifiers may include rhenium, germanium, lead, cobalt, nickel, indium, gallium, zinc, uranium, dysprosium, thallium, molybdenum or a mixture thereof. Typically, a catalytically effective amount of one or more metal modifiers may be incorporated into the catalyst by any means known in the art to effect a homogeneous or stratified distribution.

The catalyst can exhibit one or more properties. One property can be a quotient of carbon monoxide adsorption with infrared spectral detection to weight percent of a noble metal (e.g. platinum) determined by elemental analysis: (CO area)/(weight % of the noble metal). Generally, the CO area is defined as an integrated absorbance area per milligram of catalyst. Typically the catalyst exhibits a quotient of no more than about 0.10, preferably about 0.05-about 0.10, more preferably about 0.05-about 0.08, and optimally about 0.05-about 0.07. In some exemplary embodiments, a quotient can be about 0.06-about 0.10. The procedure for measuring the quotient can include grinding a sample into a fine powder and pressing the powder into about 13 millimeter (mm) diameter self-supporting pellets. Generally, the pellets are pretreated by flowing hydrogen for 2 hours at a desired temperature, e.g., about 430° C., to remove physisorbed water. Afterwards, the sample can be cooled to room temperature under pressure and a spectrum recorded for hydroxyl analysis. The carbon monoxide adsorption can be performed at 30° C. for 15 minutes on a machine sold under the trade designation Nicolet Magna 550 spectrophotometer by Thermo Nicolet of Madison, Wis. The carbon monoxide spectrum can be recorded after purging off excess gas phase carbon monoxide. Afterwards, the pretreated spectrum can be subtracted from the carbon monoxide spectrum for data analysis. Generally, the carbon monoxide peak position and area are compared within a sample set.

One exemplary process for preparing the catalyst can include providing a support. Afterwards, the support can be steamed to tailor its acid activity. That being done, a noble metal can be added to the support to form a catalyst precursor. The support can be impregnated with a water-soluble, decomposable compound of the noble metal. Next, the support can be calcined with the added noble metal. Afterwards, the calcined molecular support may be ion-exchanged with a solution. Generally, the solution includes at least one hydrogen-forming cation, which can include $NH_4^+$. The solution can be formed by combining a source of hydrogen-forming cations, such as ammonium nitrate, ammonium sulfate, and ammonium chloride, with water. Afterwards, the ion-exchanged support may be washed and/or calcined. Generally, the ion-exchange is done after impregnation with the noble metal.

Specifically, a support can be formed from a zeolite and a binder. In one exemplary embodiment, the support may be in a shape of a sphere that can be continuously manufactured by a well-known oil drop method. Generally, preparation of alumina-bound spheres involves dropping a mixture of molecular sieve, alsol, and gelling agent into an oil bath maintained at elevated temperatures. Examples of gelling agents that may be used in this process include hexamethylene tetraamine, urea, and mixtures thereof.

The gelling agents can release ammonia at an elevated temperature that sets or converts the mixture into hydrogel spheres. The spheres may be then withdrawn from the oil bath and typically subjected to specific aging treatments in oil and an ammonia solution to further improve their physical characteristics. Exemplary oil dropping methods are disclosed in U.S. Pat. No. 2,620,314 and US 2007/0060779 A1. Furthermore, the support can be in the form of other shapes, such as an extrudate or a composite structure, as disclosed in US 2007/0060779 A1. Once the support is formed, it may optionally be dried and/or calcined.

Generally, the support is subjected to steaming to tailor its acid activity. The steaming may be effected at any stage, such as steaming the binder and/or zeolite before forming support, or steaming the support before or after impregnating the support with a noble metal. Usually steaming is conducted prior to incorporating the noble metal onto the support. Steaming conditions can include a water concentration of about 1-about 100%, by volume, pressure of about 100 kPa-about 2 MPa, and a temperature of about 600-about 1200° C. Preferably, the steaming temperature is at least about 650° C., at least about 750° C., and even at least about 775° C. In some instances, a temperature of about 800-about 850° C. for at least about one hour can be utilized.

Alternatively or in addition to the steaming, the support may be washed with one or more solutions of ammonium nitrate, a mineral acid, or water. Considering the first alternative, the catalyst may be washed with a solution of about 5-about 30%, by weight, ammonium nitrate. When acid washing is employed, a mineral acid, such as HCl or $HNO_3$ is preferred. Sufficient acid can be added to maintain a pH of more than about 1-about 6, preferably about 1.5-about 4. Generally, the catalyst is maintained in a bed over which the solution and/or water is circulated for a period of from about 0.5-about 48 hours, preferably about 1-about 24 hours. The washing may be done at any stage of the preparation, and furthermore, two or more stages of washing may be employed.

If the molecular sieve is in a metal salt form, the support can be ion-exchanged with a salt solution containing at least one hydrogen-forming cation such as $NH_4^+$ or a quaternary ammonium to provide the desired acidity. The hydrogen-forming cation replaces principally alkali-metal cations to provide, after calcination, the hydrogen form of the molecular sieve component. Suitable compounds for the solute in a water solvent include ammonium nitrate, ammonium sulfate, and/or ammonium chloride.

The noble metal may be incorporated onto the support in any suitable manner that achieves the preferential deposition in the molecular sieve to form a catalyst precursor. The noble metal may be incorporated before, during or after incorporation of the optional IUPAC Group 14 element. One method of preparing the catalyst involves the utilization of a water-soluble, decomposable compound of platinum to impregnate the calcined sieve/binder composite. Alternatively, a platinum compound may be added at the time of compositing the molecular sieve component and binder. A complex of platinum that may be employed includes chloroplatinic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, and/or sodium tetranitroplatinate (II). Generally, the finished catalyst has a noble metal, such as platinum, content of no more than about 350 ppm, by weight, preferably about 150-about 350 ppm, by weight, and optimally about 300-about 350 ppm, by weight, based on the weight of the catalyst.

The IUPAC Group 14 element may be incorporated into the support in any suitable manner and may be incorporated before, during or after incorporation of the noble metal. One method of preparing the catalyst involves the utilization of a water-soluble, decomposable compound of tin to impregnate the calcined sieve/binder composite. Alternatively, a tin compound may be added at the time of compositing the molecular sieve component and binder.

The tin compound and composition of the impregnating solution can have an effect on the desired association of tin with platinum group metal. Exemplary tin compounds can include halogens, hydroxides, oxides, nitrates, sulfates, sulfites, carbonates, phosphates, phosphites, halogen-containing oxyanion salts, hydrocarbyl compounds and complexes, and carboxylate compounds and complexes, e.g., with amines and quaternary ammonium compounds. The halogen-containing oxyanion salts may include chlorates, perchlorates, and bromates. An exemplary compound may include tin dichloride, tin tetrachloride, tin oxide, tin dioxide, chlorostannous acid, tetrabutyl tin, tetraethyl tin, ammonium hexachlorostannate, or tetraethylammonium trichlorostannate.

After incorporating the noble metal and optionally IUPAC Group 14 element, the catalyst precursor may optionally be dried and/or calcined. Drying is often at a temperature of from about 100-about 320° C. for a period of about 2-about 24 or more hours and, usually, calcining is at a temperature of about 400-about 650° C. in an air atmosphere for a period of about 0.1-about 10 hours until the metallic compounds present are converted substantially to the oxide form. If desired, the optional halogen component may be adjusted by including a halogen or halogen-containing compound in the air atmosphere.

Next, the catalyst precursor can be subjected to ion-exchanging with at least one hydrogen-forming cation in a solution. Generally, the solution includes at least one hydrogen-forming cation, which can include $NH_4^+$. The solution can be formed by combining a source of hydrogen-forming cations, such as ammonium nitrate, ammonium sulfate, and ammonium chloride, with water. The ion-exchanging can include at least one wash stage, at least one rinse stage, and at least one calcining stage. Typically, the water utilized in the wash and rinse stages is deionized water.

Desirably, the ion-exchanging can include two wash stages. Generally, each stage includes washing the catalyst for generally about 1-about 10 hours, preferably about 4-about 6 hours, and optimally about 5 hours. In addition, each stage utilizes a ratio, by weight, of catalyst precursor to hydrogen forming cation solution of generally about 1:4-about 4:1, preferably about 2:1-about 1:2, and optimally about 1:1. Moreover, each stage utilizes a ratio, by weight, of catalyst precursor to water of generally about 1:1-about 1:10, preferably about 1:3-about 1:8, and optimally about 1:5.7. After agitation, the wash solution can have a pH of about 2-about 4. Generally, the solution formed in the wash stage after combining the catalyst precursor and the hydrogen-forming cation solution has a pH of about 3-about 6. During each washing stage, the catalyst precursor may be placed in the wash solution and the solution is sufficiently agitated by, e.g., an impeller. The parameters utilized in each wash stage can be the same or different. Generally, the catalyst precursor is dried for at least about 1 hour, preferably at least about 12 hours after the first wash stage.

Afterwards, the ion-exchanged catalyst precursor may be rinsed and/or calcined. Usually, the catalyst precursor is rinsed with a ratio, by weight, of the catalyst precursor to water of about 1:1-about 1:8, preferably about 1:2-about 1:6, and optimally about 1:4. The rinsing is conducted at a temperature of generally at least about 50° C., preferably at least about 70° C., and optimally at least about 85° C., for a period of generally no more than about 3 hours, preferably no more than about 1.5 hours, and optimally no more than about 0.5 hours.

Subsequently, a calcination can be conducted in one or more stages. Preferably, the calcination is conducted in two stages. The first stage can be at a temperature generally no more than 200° C., preferably about 100-about 150° C., and optimally about 120° C. for a period of no more than about 5 hours, preferably about 1-about 3 hours, and optimally about 2 hours. The second stage can be at a temperature of generally no more than about 700° C., preferably about 400-about 600° C., and optimally about 500-about 530° C. for a period of no more than about 8 hours, preferably about 2-about 6 hours, and optimally about 4 hours. Typically, the temperature is ramped from the first stage to the second stage with an air purge occurring for both stages.

The catalyst may be utilized to isomerize a feed stock including a non-equilibrium amount of at least one xylene and ethylbenzene. Generally, these aromatic compounds are in a non-equilibrium mixture, i.e., at least one C8 aromatic isomer is present in a concentration that differs substantially from the equilibrium concentration at isomerization conditions. Thus, a non-equilibrium xylene composition can exist where one or more xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feed stocks will contain meta-xylene. Generally the mixture will have an ethylbenzene content of about 1-about 60%, by weight, an ortho-xylene content of about 0-about 35%, by weight, a meta-xylene content of about 20-about 95%, by weight, and a para-xylene content of about 0-about 30%, by weight. Usually the non-equilibrium mixture is prepared by removal of para-, ortho-, and/or meta-xylene from a fresh C8 aromatic mixture obtained from an aromatic production process. The feed stocks may contain other components, including, but not limited to naphthenes and acyclic paraffins, as well as higher and lower molecular weight aromatics.

The alkylaromatic hydrocarbons may be obtained in appropriate fractions from various refinery petroleum streams, e.g., as individual components or as certain boiling-range fractions obtained by the selective fractionation and distillation of catalytically cracked or reformed hydrocarbons. Concentration of the isomerizable aromatic hydrocarbons is optional. The catalyst can isomerize the alkylaromatic-containing streams such as a catalytic reformate with or without subsequent aromatics extraction to produce specified xylene isomers and particularly to produce para-xylene.

The feedstock, in the presence of hydrogen, can be contacted with the catalyst described above. Contacting may be effected using the catalyst system in a fixed-bed system, a moving-bed system, a fluidized-bed system, and an ebullated-bed system or in a batch-type operation. Generally, a fixed-bed system is preferable. In a fixed-bed system, the feed mixture is preheated by suitable heating means to the desired reaction temperature, such as by heat exchange with another stream if necessary, and then passed into an isomerization zone containing the catalyst. The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion.

Typically, the contacting is conducted under isomerization conditions including an isomerization temperature generally about 100-about 550° C. or more, preferably about 150°-500° C. The pressure generally is from about 10 kPa-about 10 MPa, preferably about 100 kPa-about 3 MPa. The isomerization condition can include the presence of hydrogen with a hydrogen to hydrocarbon mole ratio of about 0.5:1-about 10:1, preferably about 1:1 or about 2:1-about 5:1. Generally, a sufficient mass of catalyst (calculated based upon the content of molecular sieve in the catalyst) is contained in an isomerization zone to provide a weight hourly space velocity (WHSV) with respect to the liquid feed stream (those components that are normally liquid at standard temperature and pressure) of about 0.1-about 100 $hr^{-1}$, preferably about 0.5-about 50 $hr^{-1}$, and optimally about 2-about 25 $hr^{-1}$.

The isomerization can be conducted in a liquid, a vapor or at least partially vaporous phase. For convenience in hydrogen distribution, the isomerization is preferably conducted in at least partially in the vapor phase. When conducted at least partially in the vaporous phase, the partial pressure of C8 aromatics in the reaction zone is preferably such that at least about 50%, by weight, of the C8 aromatics would be expected to be in the vapor phase. Often the isomerization is conducted with essentially all the C8 aromatics being in the vapor phase.

Usually the isomerization conditions are sufficient that at least about 10%, by weight, preferably about 20-about 90%, by weight, of the ethylbenzene in the feed stream is converted. Generally the isomerization conditions do not result in a xylene equilibrium being reached. Often, the mole ratio of xylenes in the product stream is at least about 80%, about 85% or about 99%, by mole, of equilibrium under the conditions of the isomerization. Where the isomerization process is to generate para-xylene, e.g., from meta-xylene, the feed stream can contain less than about 5%, by weight, para-xylene and the isomerization product can include a para-xylene to xylenes mole ratio of about 0.20:1-about 0.25:1, preferably at least about 0.23:1.

Any effective recovery scheme known in the art may be used to recover an isomerized product from the effluent of the isomerization zone. Typically, the isomerization product is fractionated to remove light by-products such as alkanes, naphthenes, benzene and toluene, and heavy byproducts to obtain a C8 isomer product. Heavy byproducts include dimethylethylbenzene and trimethylbenzene. In some instances, certain product species such as ortho-xylene or dimethylethylbenzene may be recovered from the isomerized product by selective fractionation. The product from isomerization of C8 aromatics usually is processed to selectively recover the para-xylene isomer, optionally by crystallization. Selective adsorption is preferred using crystalline aluminosilicates according to U.S. Pat. No. 3,201,491. Other adsorption recovery process are described in U.S. Pat. No. 4,184,943, and U.S. Pat. No. 4,402,832.

The catalyst disclosed herein may be regenerated. As an example, a regeneration process, such as disclosed in U.S. Pat. No. 6,143,941, using high temperature oxidation can remove carbonaceous material.

The elemental analysis of the catalyst components can be determined by Inductively Coupled Plasma (ICP) or Inductively Coupled Plasma-Atomic Emission Spectroscopy (ICP-AES) analysis. Particularly, some components, such as the noble metal, can be measured by digesting a one gram sample of catalyst or zeolite in a solution of hydrogen chloride, hydrogen fluoride, and hydrogen nitrate until the sample is completely digested. First, after placing the catalyst or zeolite in a solution of hydrogen chloride, hydrogen fluoride, and hydrogen nitrate, the solution temperature can be ramped for about 15 minutes from room temperature to about 150° C. in a microwave, and afterwards, held for about 10 minutes with sufficient pressure to prevent vaporization of the solution. That being done, the mixture can be cooled to room temperature. The metal composition can be analyzed by an ICP-AES instrument sold under the trade designation 3000 DV instrument by PerkinElmer of Waltham, Mass.

The other components, such as a zeolite or a binder where each may contain silica, can be measured by UOP Method 961-98.

The hydrocarbon streams associated with processes utilizing the catalyst disclosed herein can have components measured by a gas chromatograph sold by Agilent Technologies, Inc. of Palo Alto, Calif. The gas chromatograph may have two columns. The first column can be a wax column, which can be obtained from Restek Corp. of Bellefonte, Pa., providing a polarity separation of aromatic compounds. Such aromatic compounds can include xylenes, such as para-xylene, meta-xylene, and ortho-xylene; dimethylethylbenzene, such as 1-ethyl-2,3-dimethylbenzene, 1-ethyl-2,5-dimethylbenzene, 1-ethyl-3,4-dimethylbenzene, 1-ethyl-2,4-dimethylbenzene, 1-ethyl-2,6-dimethylbenzene, and 1-ethyl-3,5-dimethylbenzene; and benzene. An exemplary method used to measure these aromatic components is UOP-744-06. The non-aromatic components, such as cycloparaffins, particularly a C6 cycloparaffin, can be determined by boiling point separation via a column, which can be obtained from Agilent Technologies, Inc. of Palo Alto, Calif. Such a measurement can be made in accordance with UOP-690-99.

All the UOP methods, such as UOP-961-98, UOP-690-99, and UOP-744-06 discussed herein, can be obtained through ASTM International, 100 Barr Harbor Drive, West Conshohocken, Pa., USA.

ILLUSTRATIVE EMBODIMENTS

The following examples are intended to further illustrate the subject catalyst. These illustrations of embodiments of the invention are not meant to limit the claims of this invention to the particular details of these examples. These examples are based on engineering calculations and actual operating experience with similar processes.

Example 1

Aluminum-phosphate-bound MFI spheres are prepared substantially according to Example 1 of U.S. Pat. No. 6,143,941. A first solution is prepared by adding phosphoric acid to an aqueous solution of hexamethylenetetraamine (HMT) in an amount to yield a phosphorus content of the finished catalyst equal to about 11%, by weight. A second solution is prepared by adding a sodium-form MFI-type zeolite having an $Si/Al_2$ ratio of about 39:1 to enough alumina sol, prepared by digesting metallic aluminum in hydrochloric acid, to yield a zeolite content in the finished catalyst equal to about 67%, by weight. These two solutions are comingled to achieve a homogeneous admixture of HMT, phosphorus, alumina sol, and zeolite. This admixture is dispersed as droplets into an oil bath maintained at about 93° C. The droplets remain in the oil bath until they set and form hydrogel spheres having a diameter of about 1.6 mm. The spheres are removed from the oil bath, water washed, air dried, and calcined at a temperature of about 550° C. The calcined spheres then are subjected to steaming at a temperature of about 660° C. in an atmosphere of 100% steam in air for about 1 hour.

Subsequently, the spheres are subjected to ion-exchanging with at least one hydrogen-forming cation in a solution before metal impregnation. Particularly, the spheres are subjected to two wash stages. Each stage provides the spheres with a ratio, by weight, to deionized water and ammonium nitrate of, respectively, about 1:5.7 and about 1:1.

Generally, the first stage begins by dividing the deionized water into two portions. The first portion of the deionized water is added to the catalyst in a weight ratio of about 2.85:1 and left to cool for about 5-about 7 minutes. Afterwards, the second portion of the deionized water is added to the ammonium nitrate in a weight ratio of about 2.85:1 and is heated to about 65° C. for about 5-about 7 minutes. Next, the second portion is added to the first portion and the combined solution is heated to a temperature of about 87° C.-about 94° C., preferably about 88° C. for about 5 hours, and is sufficiently agitated, such as with an impeller at about 60 rpm. The wash solution has a pH of about 2.3-about 3.4. Afterwards, the spheres are dried about 8-about 12 hours.

After the spheres are dried, the second stage is conducted on the dried spheres. The second stage begins by dividing the deionized water into two portions. The first portion of the deionized water is added to the catalyst in a weight ratio of about 2.85:1 and left to cool for about 5-about 7 minutes. Afterwards, the second portion of the deionized water is added to the ammonium nitrate in a weight ratio of about 2.85:1 and is heated to about 65° C. for about 5-about 7 minutes. Next, the second portion is added to the first portion. The combined solution is heated at a temperature of about 87° C.-about 94° C., preferably about 88° C. for about 5 hours, and is sufficiently agitated, such as with an impeller at about 60 rpm. The wash solution has a pH of about 2.3-about 3.4. Afterwards, the spheres are dried about 8-about 12 hours.

After the spheres are washed, the spheres are subjected to rinsing. The deionized rinse water to spheres weight ratio is about 4.2:1. Desirably, the deionized water is divided into two equal parts. The first part of deionized water in a weight ratio of about 2.1:1 with respect to the spheres is placed in a container. The spheres are added to the first part of deionized water. Next, the second part of deionized water is added to the first part and the spheres. Next, sufficient agitation is provided by, e.g., an impeller at about 60 rpm. The resulting mixture is heated to about 88° C. for about 0.5 hours. The pH of the rinse water is about 2.6-about 4.1. Afterwards, spheres are dried for about 8-about 12 hours.

That being done, the spheres can be calcined. Calcination generally takes place in two stages. The first stage calcines the spheres at about 121° C. for about 2 hours. Afterwards, the temperature can be ramped upward to initiate the second stage. Generally, the second stage calcines the spheres at about 524° C. for about 4 hours. The ion-exchanging process including the washing, rinsing, and calcining may be referred hereinafter as the "ion-exchange process".

The calcined spheres are then metal-impregnated using a solution of tetraamine platinum chloride to yield a catalyst precursor with about 400 weight-ppm platinum based on the weight of the catalyst. Upon completion of the impregnation, the spheres are dried and calcined in two stages as described above.

Next, the ion-exchange process is conducted again. Thus, the ion-exchange process is conducted twice, namely once before the metal impregnation and once after the metal impregnation, to obtain an exemplary ion-exchanged catalyst.

Example 2

An ion-exchanged aluminum-phosphate-bound MFI catalyst is prepared similarly as Example 1, except the ion exchange process is only conducted after the spheres are metal impregnated, dried, and calcined, and not before the metal impregnation. Thus, the ion-exchange process is conducted only once after metal impregnation.

Example 3

Aluminum-phosphate-bound MFI spheres are prepared substantially according to Example 1 of U.S. Pat. No. 6,143,941. A first solution is prepared by adding phosphoric acid to an aqueous solution of hexamethylenetetraamine (HMT) in an amount to yield a phosphorus content of the finished catalyst equal to about 11%, by weight. A second solution is prepared by adding a sodium-form MFI-type zeolite having an $Si/Al_2$ ratio of about 39:1 to enough alumina sol, prepared by digesting metallic aluminum in hydrochloric acid, to yield a zeolite content in the finished catalyst equal to about 67%, by weight. These two solutions are commingled to achieve a homogeneous admixture of HMT, phosphorus, alumina sol, and zeolite. This admixture is dispersed as droplets into an oil bath maintained at about 93° C. The droplets remain in the oil bath until they set and form hydrogel spheres having a diameter of about 1.6 mm. The spheres are removed from the oil bath, water washed, air dried, and calcined at a temperature of about 550° C. The calcined spheres then are subjected to steaming at a temperature of about 660° C. in an atmosphere of 100% steam in air for about 1 hour.

Next, the ion-exchange process referenced-above is conducted. Afterwards, the spheres are impregnated with an aqueous solution of tin(II) chloride: ethylenediaminetetraacetic acid:ammonium hydroxide:tetra-amine platinum chloride to incorporate platinum and tin on the spheres, dried and calcined in air with 3% steam at 538° C., as disclosed in Example 1 of US 2007/0060779 A1. Thus, the spheres have about 250 weight-ppm platinum and about 2000 weight-ppm tin based on the weight of the catalyst. Such a pre-metal-impregnated ion-exchanged catalyst is made according to U.S. Pat. No. 6,143,941 and US 2007/0060779 A1.

Afterwards, the metal impregnated spheres are again subjected to the ion-exchange process. Thus, the spheres are subject to the ion exchange process before and after the metal impregnation with platinum and tin.

Example 4

A catalyst is made in accordance to Example 1, except the ion-exchange process is conducted only once before the spheres are metal impregnated, dried, and calcined. The catalyst is subsequently subjected to an oxidative steaming. Particularly, the catalyst is heated to about 400° C. for about 24 hours in an environment including about 1 mole percent steam at about 720 kPa and about 0.3 mole percent oxygen. Afterwards, the steam is continued while the temperature is ramped up to about 450° C. and held at that temperature for about 10 hours and in an environment including about 2.0 mole percent oxygen. Subsequently, the oxidatively steamed catalyst is subjected to the ion exchange process.

Comparison Example 1

An aluminum-phosphate-bound MFI catalyst is prepared as in Example 1, except the ion-exchange process is conducted only once before the spheres are metal impregnated, dried and calcined. Thus, the ion-exchange process is only conducted once. This isomerization catalyst is made according to U.S. Pat. No. 6,143,941.

Comparison Example 2

A catalyst is prepared in accordance to Comparison Example 1, and is subsequently subjected to rinsing and calcining in accordance with the ion-exchange process, but not washing.

Comparison Example 3

A catalyst is prepared in accordance to Comparison Example 1, and is subsequently subjected to calcining in accordance with the ion-exchange process, but not washing and rinsing.

Comparison Example 4

A catalyst is prepared in accordance to Example 1 of U.S. Pat. No. 6,143,941 except the steaming is at an atmosphere of 100% steam for 1 hour and the catalyst contains 400 weight-ppm platinum. Subsequently, the catalyst is subjected to washing, rinsing and calcining according to the ion exchange process, except both wash stages omit the ammonium nitrate.

Comparison Example 5

A catalyst is prepared in accordance to Example 1 of U.S. Pat. No. 6,143,941 except the steaming is at an atmosphere of 100% steam for 1 hour and the catalyst contains 400 weight-ppm platinum. Subsequently, the catalyst is subjected only to calcining, and not washing and rinsing, pursuant to the ion exchange process.

Comparison Example 6

Calcined spheres are prepared in accordance to Example 1 of U.S. Pat. No. 6,143,941 except the steaming is in an atmosphere of 100% steam for 1 hour. Afterwards, the spheres are subjected to the ion exchange process. Next, spheres are then metal-impregnated using a solution of tetraamine platinum chloride to yield a catalyst precursor with about 450 weight-ppm platinum based on the weight of the catalyst. Upon completion of the impregnation, the spheres are dried and calcined in two stages as described above.

Comparison Example 7

A catalyst is made according to U.S. Pat. No. 6,143,941 and analyzed.

Comparison Example 8

Another catalyst is made according to U.S. Pat. No. 6,143,941 and analyzed.

Comparison Example 9

A further catalyst is made according to U.S. Pat. No. 6,143,941 and analyzed.

Comparison Example 10

Yet another catalyst is made according to U.S. Pat. No. 6,143,941 and analyzed.

Comparison Example 11

Still another catalyst is made according to U.S. Pat. No. 6,143,941 and analyzed.

Properties

The examples discussed above are measured for weight percent of platinum and ratio of carbon monoxide adsorption to weight percent of platinum as discussed above. These properties are depicted in the table below:

TABLE 1

| Example Number. | Pt PPM, by weight, based on catalyst weight | Area | (CO area)/(weight % Pt) |
|---|---|---|---|
| Example 1 | 310 | 0.003 | 0.097 |
| Example 2 | 350 | 0.002 | 0.057 |
| Example 3 | 240 | 0.000 | 0.000 |
| Example 4 | 330 | 0.002 | 0.061 |
| Comparison Example 1 | 370 | 0.005 | 0.135 |
| Comparison Example 2 | 390 | 0.003 | 0.077 |
| Comparison Example 3 | 360 | 0.002 | 0.056 |
| Comparison Example 4 | 440 | 0.007 | 0.159 |
| Comparison Example 5 | 450 | 0.007 | 0.156 |
| Comparison Example 6 | 450 | 0.008 | 0.178 |
| Comparison Example 7 | 390 | 0.010 | 0.256 |
| Comparison Example 8 | 380 | 0.008 | 0.211 |
| Comparison Example 9 | 380 | 0.007 | 0.184 |
| Comparison Example 10 | 350 | 0.007 | 0.200 |
| Comparison Example 11 | 380 | 0.006 | 0.158 |

As depicted, Example 3, containing tin, has no measurable carbon monoxide absorbance.

Performance

The catalysts from Table 1 are placed in a pilot plant flow reactor. The reactor processes a non-equilibrium C8 aromatic feed having the following approximate composition, in percent, by weight:

TABLE 2

Feed Composition

| Component | Percent, By Weight |
|---|---|
| Ethylbenzene | 7.3 |
| Para-xylene | 0.7 |
| Meta-xylene | 70.0 |
| Ortho-xylene | 22.0 |

This feed is contacted with each catalyst depicted below at a pressure of about 1300 kPa, a WHSV of about 10 hr$^{-1}$, and a hydrogen/hydrocarbon mole ratio of about 4:1. The catalysts are reduced in the reactor prior to processing the feed.

Several process measurements are made, such as the weight average bed temperature (WABT) and the benzene purity (BP), at about 70%, by weight, ethylbenzene (EB) conversion. The BP is the weight percent of benzene on a C6 cycloparaffin or naphthene (C6N) basis. The BP is calculated as follows:

BP, C6N=(Benzene weight %)/(Benzene weight %+C6N weight %)*100

Other measurements include the mole percent of para-xylene (pX %) per xylene in a product stream, and can be calculated as:

pX %=pX/X*100%, where:

pX represents moles of para-xylene in the product;
X represents moles of xylene in the product.

Other measurements taken can include dimethylethylbenzene (DMEB) yield and xylene loss (XL). The DMEB yield is the sum of weight percent yield for the six isomers in the product. These isomers are 1-ethyl-2,3-dimethylbenzene, 1-ethyl-2,5-dimethylbenzene, 1-ethyl-3,4-dimethylbenzene, 1-ethyl-2,4-dimethylbenzene, 1-ethyl-2,6-dimethylbenzene, and 1-ethyl-3,5-dimethylbenzene and can be determined by the method UOP-744-06. The DMEB yield is the sum of the yield, by weight percent, of these six isomers. XL can be determined by the formula:

XL=[(weight % xylenes feed)−(weight % xylenes product)]/[(weight % xylenes feed)]*100 where the amount of the xylenes can be determined by UOP-744-06.

The data collected is presented below:

TABLE 3

| Example Number. | WABT | BP, C6N (Weight %) | pX % | DMEB Yield | Xylene Loss |
|---|---|---|---|---|---|
| Example 1 | 376 | 98.6* | 23.7* | 0.02* | 3.3* |
| Example 2 | 378 | 98.3* | 23.6* | 0.03* | 3.1* |
| Example 3 | 391 | 99.9* | 23.5* | 0.13* | 2.8* |
| Example 4 | 399 | 99.0* | 23.6* | 0.01* | 1.9* |
| Comparison Example 1 | 374 | 95.3* | 23.7* | 0.01* | 2.8* |
| Comparison Example 2 | 380 | 97.9* | 23.8* | 0.03* | 3.9* |
| Comparison Example 3 | 375 | 97.4* | 23.7* | 0.03* | 2.8* |
| Comparison Example 4 | 387 | 96.6* | 23.8* | 0.03* | 4.0* |
| Comparison Example 5 | 394 | 96.1* | 23.6* | 0.03* | 3.4* |
| Comparison Example 6 | 378 | 94.5* | 23.7* | 0.02* | 2.7* |
| Comparison Example 7 | 384 | 89.6 | 23.7 | 0.01 | 2.2 |
| Comparison Example 8 | 376 | 93.8 | 23.8 | 0.02 | 4.4 |
| Comparison Example 9 | 378 | 93.8 | 23.9 | 0.02 | 2.6 |
| Comparison Example 10 | 374 | 94.4* | 23.7* | 0.02* | 2.4* |
| Comparison Example 11 | 397 | 97.9 | 23.9 | 0.03 | 7.1 |

*The benzene purity, para-xylene mole percent, dimethylethylbenzene yield, and xylene loss of these asterisked values are determined by online gas chromatography measurements. The gas chromatography instrument can be an instrument sold under the trade designation model 6890 by Agilent of Palo Alto, CA, as discussed above. Otherwise the benzene purity, para-xylene mole percent, dimethylethylbenzene yield, and xylene loss in the other values are determined by offline analysis utilizing procedures UOP-744-06 and UOP-690-99.

As depicted above, catalysts of Examples 1-4 have a (CO area)/(weight % of platinum) quotient of no more than about 0.10 and produce a benzene purity of at least about 98.3%. Referring to Table 1, Examples 1, 2 and 4, in particular, can have a (CO area)/(weight % of platinum) quotient of about 0.06-about 0.1. Moreover, such a benefit is accomplished with a platinum content of about 310-about 350 ppm. In contrast, the catalyst of Comparison Example 10 has a platinum content of about 350 ppm, but a benzene purity of 94.4%. Generally, catalysts prepared by methods as discussed above can improve benzene purity.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An ion-exchanged xylene isomerization catalyst, comprising:
    about 1-about 99%, by weight, of at least one of MFI, MEL, EUO, FER, MFS, MTT, MTW, TON, MOR, and FAU zeolite;
    about 1-about 99%, by weight, of a binder comprising an aluminum phosphate; and
    a metal component consisting essentially of a noble metal component and an optional metal modifier, the noble metal component is present in a positive amount no more than about 350 ppm, by weight, of a noble metal based on the weight of the catalyst, and the optional metal modifier is selected from the group consisting of rhenium, germanium, lead, cobalt, nickel, indium, gallium, zinc, thallium, and combinations thereof; wherein the catalyst has a quotient of (CO area)/(weight % of the noble metal) of no more than about 0.10.

2. The ion-exchanged xylene isomerization catalyst according to claim 1, wherein the catalyst comprises about 150-about 350 ppm, by weight of the noble metal.

3. The ion-exchanged xylene isomerization catalyst according to claim 1, wherein the noble metal comprises platinum.

4. The ion-exchanged xylene isomerization catalyst according to claim 1, wherein the catalyst comprises:
    about 10-about 90%, by weight, of the binder; and
    about 10-about 90%, by weight, of the zeolite.

5. The ion-exchanged xylene isomerization catalyst according to claim 1, wherein the catalyst has a quotient of (CO area)/(weight % of the noble metal) of about 0.05-about 0.10.

6. The ion-exchanged xylene isomerization catalyst according to claim 1, wherein the catalyst has a quotient of (CO area)/(weight % of the noble metal) of about 0.05-about 0.08.

7. The ion-exchanged xylene isomerization catalyst according to claim 1, wherein the catalyst has a quotient of (CO area)/(weight % of the noble metal) of about 0.05-about 0.07.

8. The ion-exchanged xylene isomerization catalyst according to claim 7, wherein the noble metal comprises platinum.

9. The ion-exchanged xylene isomerization catalyst according to claim 8, wherein the at least one zeolite comprises MFI.

10. The ion-exchanged xylene isomerization catalyst according to claim 9, wherein the catalyst has a quotient of (CO area)/(weight % of platinum) of about 0.06-about 0.10.

11. An ion-exchanged xylene isomerization catalyst, comprising consisting essentially of:
    about 10-about 90%, by weight, of an MFI zeolite;
    about 10-about 90%, by weight, of an aluminum phosphate binder; and
    about 150-about 350 ppm, by weight, of platinum based on the weight of the catalyst wherein the catalyst has a quotient of (CO area)/(weight % of platinum) of no more than about 0.10.

12. A process for isomerizing a non-equilibrium feed mixture of one or more xylenes and ethylbenzene, comprising:
    contacting the feed mixture with an ion-exchanged xylene isomerization catalyst to obtain an isomerized product comprising a higher proportion of para-xylene than in the feed mixture, wherein the ion-exchanged xylene isomerization catalyst comprises:
    about 1-about 99%, by weight, of at least one of MFI, MEL, EUO, FER, MFS, MTT, MTW, TON, MOR, and FAU zeolite;
    about 1-about 99%, by weight, of a binder comprising an aluminum phosphate; and
    a metal component consisting essentially of a noble metal component and an optional metal modifier, the noble metal component is present in a positive amount no more than about 350 ppm, by weight, of a noble metal based on the weight of the catalyst, and the optional metal modifier is selected from the group consisting of rhenium, germanium, lead, cobalt, nickel, indium, gallium, zinc, thallium, and combinations thereof; wherein the catalyst has a quotient of (CO area)/(weight % of the noble metal) of no more than about 0.10.

13. The process according to claim 12, wherein the catalyst has a quotient of (CO area)/(weight % of the noble metal) of about 0.05-about 0.10.

14. The process according to claim 12, wherein the contacting is conducted in the presence of hydrogen.

15. The process according to claim 12, wherein a temperature of the contacting is about 350-about 500° C.

16. The process according to claim 12, wherein a pressure of the contacting is about 100 kPa-about 5 MPa.

17. The process according to claim 12, wherein the isomerized product has a benzene purity of at least about 98.3% on a C6 naphthene basis at an ethylbenzene conversion of about 70%.

18. The process according to claim 12, wherein the contacting is at a temperature of about 350-about 500° C., a pressure of about 100 kPa-about 5 MPa, a mass hourly space velocity of about 0.1-about 100 $hr^{-1}$, and a hydrogen-to-hydrocarbon mole ratio of about 0.5:1-about 10:1.

19. The process according to claim 12, wherein the noble metal comprises platinum and the catalyst has a quotient of (CO area)/(weight % of platinum) of about 0.05-about 0.08.

20. The process according to claim 12, wherein the noble metal comprises platinum.

* * * * *